US010234383B2

(12) United States Patent
Wang et al.

(10) Patent No.: US 10,234,383 B2
(45) Date of Patent: Mar. 19, 2019

(54) TERAHERTZ SPECTRAL IMAGING SYSTEM AND SECURITY SURVEILLANCE SYSTEM EMPLOYING THE SAME

(71) Applicant: KONICA MINOLTA LABORATORY U.S.A., INC., San Mateo, CA (US)

(72) Inventors: Leiming Wang, Foster City, CA (US); Jun Amano, Foster City, CA (US)

(73) Assignee: KONICA MINOLTA LABORATORY U.S.A., INC., San Mateo, CA (US)

( * ) Notice: Subject to any disclaimer, the term of this patent is extended or adjusted under 35 U.S.C. 154(b) by 0 days.

(21) Appl. No.: 15/628,566

(22) Filed: Jun. 20, 2017

(65) Prior Publication Data

US 2018/0364158 A1    Dec. 20, 2018

(51) Int. Cl.
| G01N 21/35 | (2014.01) |
| G01N 21/3581 | (2014.01) |
| G06K 9/00 | (2006.01) |
| G01J 3/12 | (2006.01) |

(Continued)

(52) U.S. Cl.
CPC ........ *G01N 21/3581* (2013.01); *G01J 3/1256* (2013.01); *G06K 9/0063* (2013.01); *G01J 3/108* (2013.01); *G01J 2003/423* (2013.01)

(58) Field of Classification Search
CPC ............................ G01N 21/3581; G01J 3/1256
See application file for complete search history.

(56) References Cited

U.S. PATENT DOCUMENTS 8,035,083 B1    10/2011    Kozlov et al.
8,948,501 B1 *   2/2015    Kim ..................... G01S 7/4808
                                                        345/419

(Continued)

FOREIGN PATENT DOCUMENTS

CN    203674350 U    6/2014

OTHER PUBLICATIONS

Redo-Sanchez et al., "Terahertz time-gated spectral imaging for content extraction through layered structures", Nature Communications, 7:12665, Sep. 9, 2016.

(Continued)

*Primary Examiner* — Hugh Maupin
(74) *Attorney, Agent, or Firm* — Chen Yoshimura LLP (57) ABSTRACT

A terahertz (THz) spectral imaging system includes a THz 2D imaging camera, a tunable THz bandpass filter before the THz camera, and a broadband THz light source. The tunable THz bandpass filter includes a visible or infrared laser source, a spatial light modulator modulating the light to generate a spatially structured light pattern, and a semiconductor plate onto which the light pattern is projected. The light pattern generates carriers in the semiconductor plate to turn it into a metamaterial THz bandpass filter, which is tunable by changing the light patterns. A controller controls the light patterns and the THz camera in a timing sequence to acquire multiple 2D THz images at different THz frequencies. Such THz spectral image data can be further combined with visible images and LiDAR images in a security surveillance system to automatically detect security threats using image fusion and deep learning techniques.

16 Claims, 5 Drawing Sheets

(51) Int. Cl.
*G01J 3/10* (2006.01)
*G01J 3/42* (2006.01)

(56) References Cited

U.S. PATENT DOCUMENTS

| | | | |
|---|---|---|---|
| 2011/0058084 A1* | 3/2011 | Hine | G06F 3/017 |
| | | | 348/333.1 |
| 2013/0314765 A1* | 11/2013 | Padilla | G01K 7/003 |
| | | | 359/315 |
| 2014/0028457 A1 | 1/2014 | Reinpoldt | |
| 2017/0150903 A1* | 6/2017 | Barnes | A61B 5/742 |
| 2017/0256665 A1* | 9/2017 | Moon | H01L 31/0224 |
| 2017/0329127 A1* | 11/2017 | Liu | G02B 26/0816 |

OTHER PUBLICATIONS

Ali et al., "Dynamic lithography of v-shaped antennas for beam steering applications", Proceedings of SPIE, vol. 9102, p. 91020A, 2014.

Kermani et al., "Metamaterial Terahertz bandpass filters: a comparison between metallic and graphene-based structures", PIERS Proceedings, Prague, Czech Republic, Jul. 6-9, 2015, pp. 1472-1474.

Paul et al., "Highly Selective Terahertz Bandpass Filters Based on Trapped Mode Excitation", Optics Express, vol. 17, No. 21, 18590, Oct. 12, 2009.

MacDonald et al., "Spectral Transmittance of Lossy Printed Resonant-Grid Terahertz Bandpass Filters", IEEE Transactions on Microwave Theory and Techniques, vol. 48, No. 4, Apr. 2000.

Kowalski et al., "Hidden Object Detection System Based on Fusion of THz and VIS Images", Acta Physica Polonica A, vol. 124, No. 3, 2013, pp. 490-493.

Withayachumnankul et al., "Metamaterials in the Terahertz Regime", IEEE Photonics Journal, vol. 1, No. 2, Aug. 2009, pp. 99-118.

* cited by examiner

TERAHERTZ SPECTRAL IMAGING SYSTEM AND SECURITY SURVEILLANCE SYSTEM EMPLOYING THE SAME

BACKGROUND OF THE INVENTION

Field of the Invention

This invention relates to a terahertz (THz) spectral imaging system, and to an intelligent security surveillance system employing the THz spectral imaging system in combination with other imaging and data processing techniques.

Description of Related Art

Terahertz (THz) or sub-millimeter wave represents electromagnetic radiation in the spectral range between microwave and long-wave infrared (about 0.1-10 THz). THz radiation is readily transmitted through many non-metallic objects such as cardboard, wood, plastic, and textile. On the other hand, many materials of interest for security applications including weapons (metal), explosives, and chemical and biological agents have characteristic spectral fingerprints in the THz region, making THz spectral imaging a promising technique for non-destructive and non-invasive detection of hidden threats to public safety.

Compared with visible and infrared imaging, spectral imaging in THz range is relatively under-developed, due to a lack of tunable narrowband THz light sources or tunable THz bandpass filters.

An example of THz time-domain spectroscopy (THz-TDS) is described in Albert Redo-Sanchez et al., "Terahertz time-gated spectral imaging for content extraction through layered structures", Nature Communication, Vol 7, p 12665, 2016 ("Redo-Sanchez et al. 2016"). However, this is not a direct imaging technique, and requires raster scan over the sample to form a 2-dimensional (2D) image. Furthermore, it is limited to pump-probe type pulsed operation, and requires tedious post-processing such as Fourier transform to extract spectral information.

Frequency-domain THz spectral imaging based on a tunable THz source is described in U.S. Pat. No. 8,035,083, entitled "Terahertz tunable sources, spectrometers, and imaging systems." The imaging system employs a 2D THz imager and a tunable narrowband THz source. While this technology achieves THz spectral imaging, it requires a substantially monochromatic or narrowband tunable THz source, which is difficult to realize.

Chinese Patent No. CN 203674350U, entitled "Tunable terahertz wave filtering device," describes a tunable terahertz wave filtering device which uses a first THz wave dispersion device to disperse the THz light, passes the dispersed light through a THz wave filtering device which selectively transmits THz light based on spatial location, and then recombines the dispersed light using a second, complementary THz wave dispersion device. The THz wave filtering device is a semiconductor wafer such as a silicon wafer, which is transparent to the THz light when not irradiated with an excitation light. When a region of the wafer is irradiated with an excitation light, the light is absorbed and produces large amounts of photo-generated carriers in the irradiated region of the wafer; such regions block THz light because of the carriers. Tunable terahertz wave filtering is thus accomplished by optically controlling the excitation light, using an excitation light beam deflection device, to irradiate selected regions of the wafer thereby blocking THz light of selected wavelengths.

Tamelia Ali et al., "Dynamic lithography of v-shaped antennas for beam steering applications," Proceedings of SPIE Vol. 9102, p. 91020A, 2014, describes a method for generating an optical metasurface for beam steering of THz radiation: "we use a pump-probe technique, where the pump beam is used to project patterns of v-shaped antennas on the surface of a silicon substrate. In the areas illuminated with the images of v-shaped antennas electron-hole pairs are created. Therefore, the antenna structures on silicon will have metallic-like properties, we classify this structure as a metasurface. The THz beam probes refraction and reflection on the metasurface generated on the silicon substrate. The dynamic change of these patterns of metasurface causes the beam steering effects of THz radiation." (Abstract.)

Metamaterial Terahertz bandpass filters have been described. For example, M. Bana Kermani et al., "Metamaterial Terahertz bandpass filters: a comparison between metallic and graphene-based structures," PIERS Proceedings, Prague, Czech Republic, Jul. 6-9, 2015, p. 1472, describes a metamaterial-based optoelectronic THz filter: "In this article we present a design procedure to obtain voltage-dependent carrier density control in a GaN-based heterostructure with a Schottky gate configuration which serves as the substrate for a THz bandpass filter (BPF). The introduced structure consists of a cross shaped metallic layer on the AlGaN/GaN heterostructures. Then, we investigate tuning of transmission properties and the tunability of the filter. An overall tunability of about 103 GHz in the resonance frequency was obtained by varying the applied voltage from −8V to 2V. Also, a plasmonic metamaterial based on the graphene cross-shaped structure is studied and a comparison has been performed between the optical properties of graphene-based cross-shaped structure and the original structure." (Abstract.)

Oliver Paul et al., "Highly Selective Terahertz Bandpass Filters Based on Trapped Mode Excitation," Optics Express, Vol. 17, No. 21, 18590, 12 Oct. 2009, describes two types of metamaterial-based spectral bandpass filters for the terahertz (THz) frequency range, one being cross-slot structure and the other being two layers of wire-and-plate structure. "The functional structures are embedded in films of benzocyclobutene (BCB) resulting in large-area, free-standing and flexible membranes with low intrinsic loss." (Abstract.) Michael E. MacDonald et al., "Spectral Transmittance of Lossy Printed Resonant-Grid Terahertz Bandpass Filters," IEEE Transactions on Microwave Theory and Techniques, Vol. 48, No. 4, April 2000 ("MacDonald et al. 2000"), describes "terahertz bandpass filters composed of resonant arrays of crossed slots in lossy metal films deposited on dielectric membranes." (Abstract.) This paper mentions that the resonant wavelength is dependent on the size of the cross shape.

U.S. Pat. Appl. Pub. No. 2014/0028457, entitled "Real time threat detection system," describes a "real-time threat detection system incorporating a plurality of sensors adapted to detect radiation across the majority of the electromagnetic spectrum. The system also includes an aided or automatic target recognition module which compares the data from the sensors against known radiation signatures and issues an alert when an anomalous signature is detected. The system further includes an operator station which displays sensor information allowing the operator to intervene. The sensors detect radiation which is normally emitted by persons or other bodies and display areas to the operator where normal emissions are blocked." (Abstract.)

M. Kowalski et al., "Hidden Object Detection System Based on Fusion of THz and VIS Images," Acta Physica Polonica A, Vol. 124 (2013), p. 490 ("Kowalski et al. 2013"), describes fusing a visible light (VIS) image and a THz image of the same target to generate an image where the threat detected in the THz image is superimposed on the VIS image so that it is more suitable for human perception for visualizing the location of the threat.

SUMMARY

The present invention is directed to a THz spectral imaging system, as well as an intelligent security surveillance system employing the THz spectral imaging system in combination with other imaging and data processing techniques.

An object of the present invention is to provide a technique and system that enables real-time detection of many types of security threats including weapons, explosives, and other chemical and biological agents.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a terahertz (THz) spectral imaging system, which includes: a THz 2-dimensional (2D) imaging camera; a tunable THz bandpass filter comprising: a visible or infrared (IR) light source for generating a visible or IR light; a spatial light modulator receiving the visible or IR light and modulating it to generate spatially structured light patterns; and a semiconductor plate, wherein the spatial light modulator projects the light patterns onto the semiconductor plate, wherein the light pattern is configured to photo-generate carriers in the semiconductor plate to form a metamaterial THz bandpass filter in the semiconductor plate; and a control device coupled to the THz 2D imaging camera and the tunable THz bandpass filter, wherein the semiconductor plate is disposed in front of the THz 2D imaging camera to filter the THz light before it is received by the THz 2D imaging camera, and wherein the control device is configured to control the spatial light modulator to generate a plurality of predefined light patterns each corresponding to a transmission spectrum of the metamaterial THz bandpass filter, and to control a timing sequence of the spatial light modulator and the THz 2D imaging camera to acquire a plurality of 2D THz images corresponding to the plurality of predefined light patterns projected on the semiconductor plate.

In another aspect, the present invention provides a tunable THz bandpass filter which includes: a visible or infrared (IR) light source for generating a visible or IR light; a spatial light modulator receiving the visible or IR light and modulating it to generate spatially structured light patterns; and a semiconductor plate, wherein the spatial light modulator projects the light patterns onto the semiconductor plate, wherein the light pattern is configured to photo-generate carriers in the semiconductor plate to form a metamaterial THz bandpass filter in the semiconductor plate; and wherein the spatial light modulator is configured to be controlled by an external control device to generate a plurality of different light patterns to form metamaterial THz bandpass filters with different transmission spectrum in the semiconductor plate.

In another aspect, the present invention provides a security surveillance system which includes: a visible light imaging camera generating visible light images; a terahertz (THz) spectral imaging system generating a plurality of 2-dimensional (2D) THz images each based on THz light of a different frequency range; a Light Detection and Ranging (LiDAR) system generating LiDAR images representing distances of objects from a sensor of the LiDAR system; a central control and data processing system; and an alarm system, where the central control and data processing system is coupled to the visible light imaging camera, the THz spectral imaging system, the LiDAR system and the alarm system, and is configured to: perform spectral analysis of the 2D THz images to generate processed THz image indicating presence of any one of a plurality of predefined materials, fuse the visible light images, the processed THz images and the LiDAR images into a fused image, and automatically analyze the fused image using machine learning to generate an alarm based on learned behavior patterns of targets in the fused image.

In other aspects, the present invention provides methods for operating the above systems.

It is to be understood that both the foregoing general description and the following detailed description are exemplary and explanatory and are intended to provide further explanation of the invention as claimed.

DETAILED DESCRIPTION OF PREFERRED EMBODIMENTS

Embodiments of the present invention provide a THz spectral imaging system based on a dynamically tunable metamaterial THz bandpass filter.

Other embodiments of the present invention provide an intelligent security surveillance system based on the THz spectral imaging system. The system includes a THz spectral imaging system, a visible light imaging system, and a Light Detection and Ranging (LiDAR) system, and employs image fusion techniques as well as machine learning to perform threat detection and prediction.

Figure 1:
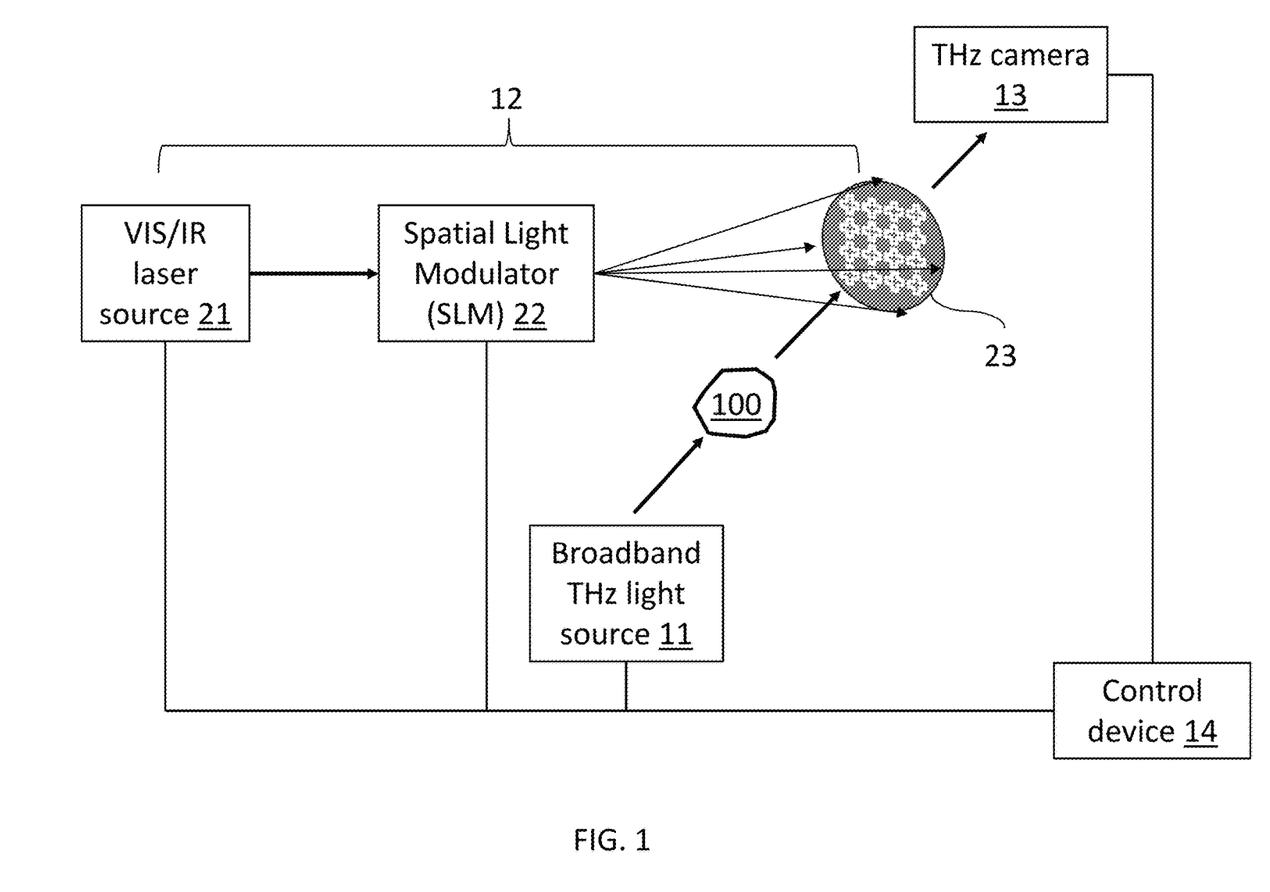
FIG. 1 schematically illustrates a THz spectral imaging system according to an embodiment of the present invention.

FIG. 1 schematically illustrates a THz spectral imaging system according to an embodiment of the present invention. As shown in FIG. 1, the THz spectral imaging system includes a broadband THz light source 11 (optional, i.e., the system can use passive or active imaging), a tunable THz bandpass filter 12, a THz 2D imaging camera 13, and a control device 14. The tunable THz bandpass filter 12 includes a visible and/or IR (VIS/IR) light source 21 (e.g. a Ti:Sapphire laser), a spatial light modulator (SLM) 22 (e.g. a digital micromirror device, DMD), and a silicon plate (also referred to as a substrate or a wafer) 23. A broadband THz light generated by the THz light source 11 illuminates an object 100, and the reflected or transmitted THz light is passed through the silicon substrate 23 (bandpass filter) for wavelength selection, before it is collected by the THz camera 13 to form an image. The THz camera 13 uses a 2D THz sensor to form a 2D image without requiring a raster scan.

The control device 14, which may include one or more processors with memories storing computer-executable programs, one or more chips or other logic circuitry, is coupled to the VIS/IR light source 21, the SLM 22, the broadband THz light source 11, and the THz camera 13 to control these components. More specifically, the control device 14 controls the operation of these components according to desired timing sequences.

The tunable THz bandpass filter 12 operates as follows. The VIS/IR light beam from the VIS/IR light source 21 is input into the SLM 22 to generate a spatially structured (i.e. modulated) light beam. An SLM, which is a device commonly used in projectors, can modulate the input light beam according to input image data (including moving image data) to generate an output beam that has a spatial variation of light intensity that corresponds to the input image data. Here the input image data may be supplied by the control device 14 or generated by the SLM 22 itself.

The spatially structured light beam from the SLM 22 is projected onto the surface of the silicon substrate 23 to form a pattern of illumination on the silicon substrate. The SLM 22 includes suitable optical components such as projection lenses to focus the light onto the silicon surface. In some embodiments, the illumination pattern includes an array of periodic elements having sizes in the nanometer to millimeter range. Photogenerated carriers in the illuminated areas on the silicon surface turn those areas into a metallic-like substance for the THz frequency (wavelength) light. As a results, the spatially structured light illumination on the silicon substrate creates an array of structural elements (referred to as THz antennas) in the silicon substrate, forming a metamaterial that functions as a THz bandpass (i.e. wavelength selective) filter. The transmission spectrum of the silicon substrate 23 (the THz bandpass filter) is determined by the size and/or shape of the metamaterial antenna elements and/or the period of the array, which is in turn determined by the image projected by the SLM 22 onto the silicon substrate 23. By providing input image data to the SLM 22 that changes with time, the pattern of illumination on the silicon substrate 23 varies with time, creating a THz bandpass filter having a temporally varying transmission spectrum.

In one embodiment of the present invention, the antenna array formed in the silicon substrate 23 includes an array of cross-shaped elements where the cross-shaped areas are not illuminated (or illuminated with a weaker intensity) and the other areas on the substrate are illuminated (or illuminated with a higher intensity than in the cross shape). In embodiments of the present invention, the transmission spectrum can be tuned by changing one or more of: the size and shape of the cross-shaped elements, the period of the array, the illumination light intensity, etc.

The dependency of THz spectral resonance on structural size, shape, periodicity, etc. of the metamaterials has been described in literature. For example, MacDonald et al. 2000 describes that, among other factors, for a cross-shaped slot array, the length of the cross shape (i.e. the length of the strokes of the cross) determines the resonance wavelength and the width of the cross shape (i.e. the width of the strokes) determines the width of resonance frequency response curve.

Figure 5:
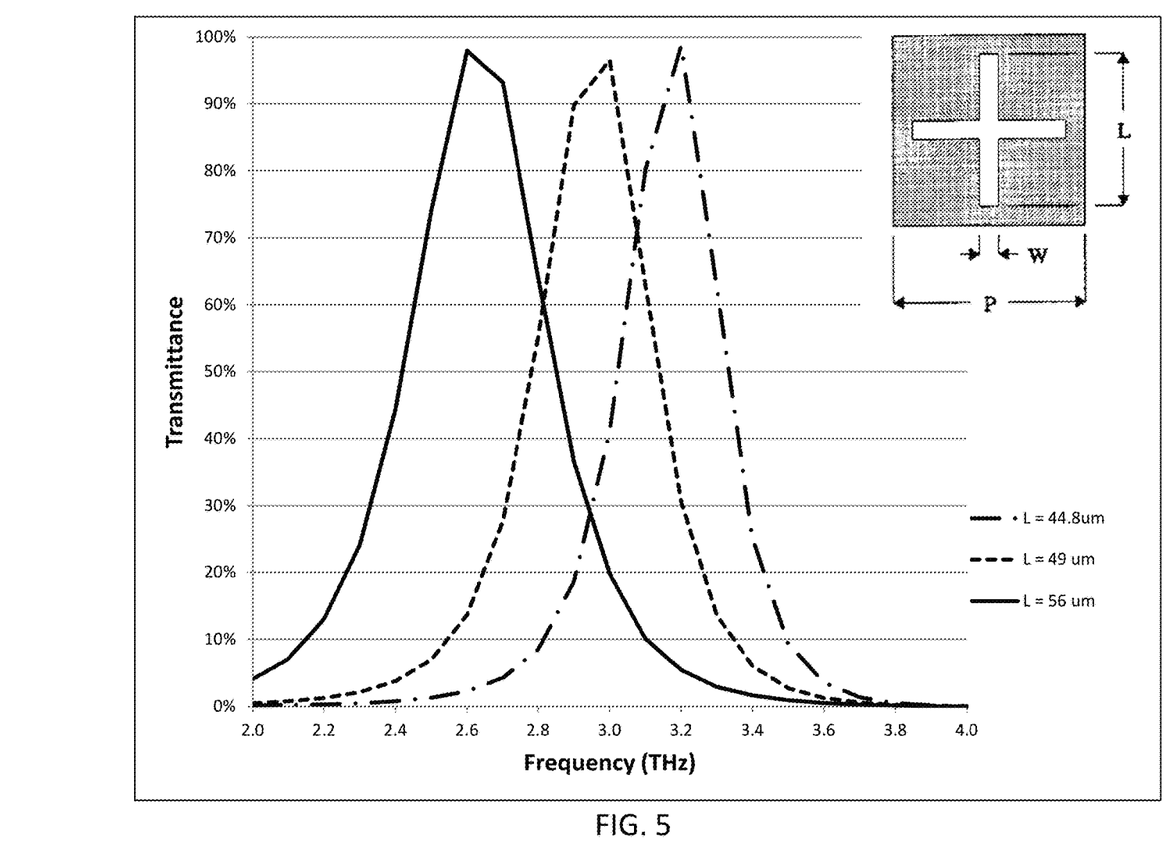
FIG. 5 schematically illustrate simulated transmission spectra for an infinite periodic array of cross-shaped slits in a perfect electric conductor using different parameters.

The inventor calculated simulated transmission spectra for an infinite periodic array of cross-shaped slits in a perfect electric conductor, shown in FIG. 5. The shape and dimensions of the cross shape is defined in the insert of FIG. 5. With the period of the array being P=70 μm and the width of the cross shape being W=7 μm, three spectral curves respectively corresponding to different cross size parameter L are shown. The simulation was done with finite element method using commercial software COMSOL Multiphysics.

Figure 2:
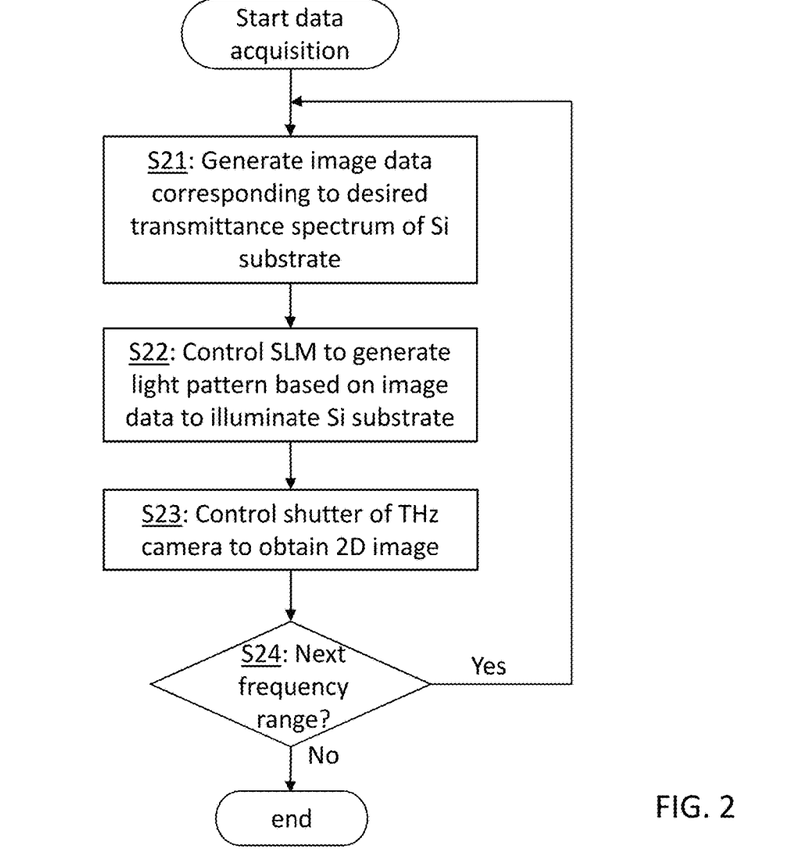
FIG. 2 schematically illustrates an operation of the THz spectral imaging system of the embodiment of FIG. 1.

In operation (see FIG. 2), the control device 14 controls the shutter timing of the THz camera 13 and the change of the light illumination pattern generated by the SLM 22 according to a defined timing sequence to acquire multiple THz images corresponding to different frequencies of THz light. In one example, the control device 14 controls the SLM 22 to generate a light illumination pattern which will produce a desired transmission spectrum of the silicon substrate 23 (steps S21 and S22); and simultaneously or with a desired time delay and while the light illumination pattern is maintained, the control device controls the THz camera 13 to acquire a 2D THz image (S23). The control device then controls the SLM to generate another light illumination pattern which produces another transmission spectrum of the silicon substrate, and controls the THZ camera to acquire another 2D THz image. This process continues until a satisfactory number of images covering a desired THz frequency range are obtained (step S24). This way, the THz images obtained by the THz camera are correlated with the frequency of the THz light as selected by the metamaterial THz bandpass filter.

The system may be controlled to operate in a continuous mode or a pulsed mode. In the continuous mode, the visible or IR laser light source 21 is continuously on and the spatially structured light beam from the SLM 22 is continuously illuminated on the silicon substrate while the pattern of illumination varies with time. In the pulsed mode, the SLM 22 generates short, discrete pulses of light (e.g., of durations in the nanosecond range), which can be achieve either by a pulsed light source 21 or by gating the SLM 22; the THz camera 13 is gated to only captures images within the pulse durations when the silicon substrate 23 is illuminated. If the broadband THz light source 11 is used for imaging, it can be continuously on, or pulsed synchronously with the illumination of the silicon substrate as well. In the continuous mode of operation, the silicon substrate is continuously illuminated and the THz camera is gated.

In the above manner, by systematically tuning the transmission spectrum of the THz bandpass filter (i.e., by programming the SLM to systematically change the light pattern illuminated on the silicon substrate) and by synchronized THz image acquisition, a series of 2D images corresponding to different THz frequencies is obtained. Thus, THz spectral imaging is achieved.

Compared to THz time-domain spectroscopy (THz-TDS) described in Redo-Sanchez et al. 2016, frequency-domain direct imaging using a 2D THz camera significantly simplifies the image acquisition and signal processing. In the mean time, using a dynamically tunable metamaterial THz bandpass filter eliminates the need (as in the system described in U.S. Pat. No. 8,035,083) for a narrowband tunable THz source for THz spectral imaging.

Figure 3:
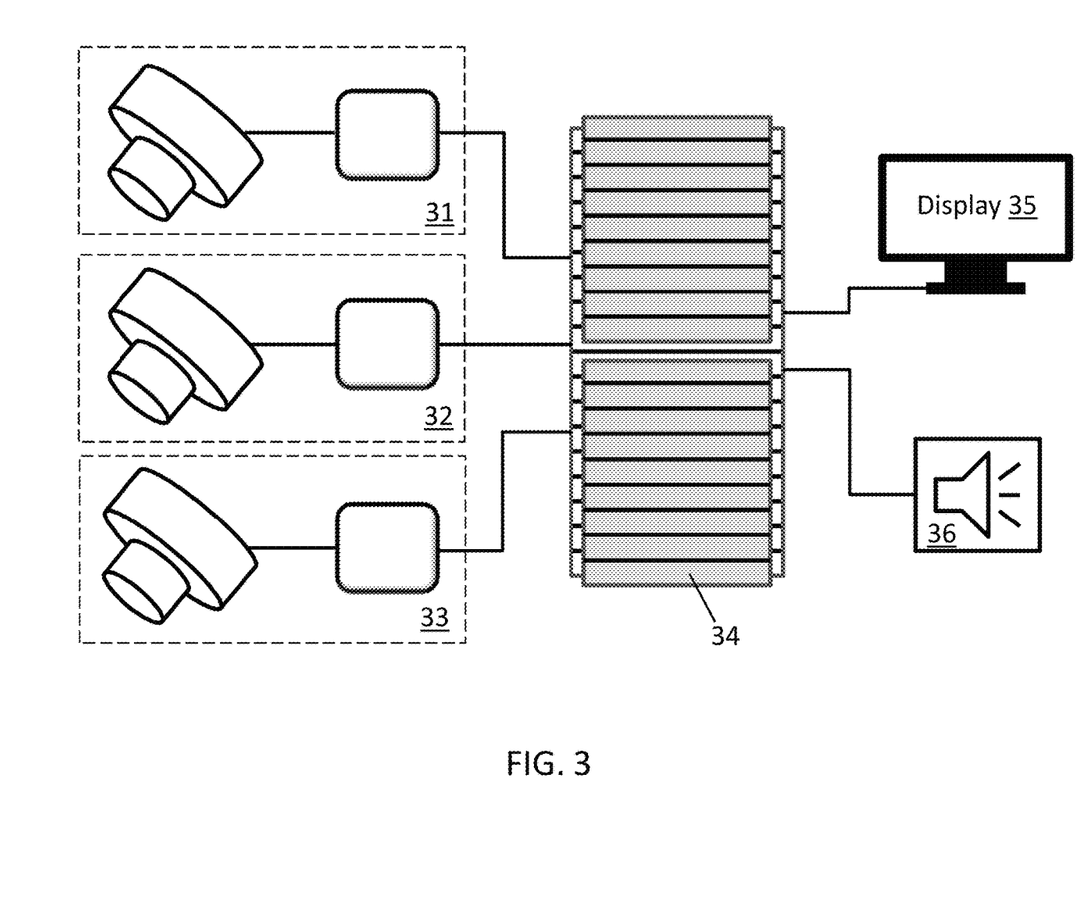
FIG. 3 schematically illustrates an intelligent security surveillance system using THz spectral imaging, image fusion techniques and deep learning techniques according to another embodiment of the present invention.

Another embodiment of the present invention provides an intelligent security surveillance system which uses THz spectral imaging and image fusion as well as machine learning techniques for threat detection and prediction. As shown in FIG. 3, the intelligent security surveillance system includes a visible light (VIS) imaging system 31, a THz spectral imaging system 32 (such as the system shown in FIG. 1), a Light Detection and Ranging (LiDAR) system 33, a central control and data processing system (e.g. one or more computers, containing processors with memory such as RAM and ROM storing computer-executable programs) 34, a display device 35, and an alarm device 36. Systems/devices 31, 32, 33, 35 and 36 are connected to the central control and data processing system 34. The central control and data processing system 34 controls the VIS imaging system 31, the THz spectral imaging system 32 and the LiDAR system 33 to acquire three respective sets of 2D images of target objects or scene, fuses or otherwise combines the images together, and then applies deep leaning techniques to process the fused images to determine whether and where security threats are present in the targets or scene. The display device 35 may be used to display the various images and/or an image of the detected threats. The alarm system 36 may be used to generate an audible or other form of alarm when threats are detected.

A LiDAR is a detection and ranging system that can measure the distances from a target to the sensor by shining a pulsed laser beam on the target and measuring the reflected pulses. The measured distance data can be used to produce 2D images where shades of color encode the distance information (referred to as a 3D image). Such images can be achieved using scanning LiDAR systems or non-scanning LiDAR systems. Solid-state LiDARs use solid state photo-detectors as the light detector.

In the intelligent security surveillance system shown in FIG. 3, the VIS imaging system 31 produces high resolution visible light images of the target scene; the THz spectral imaging system can detect hidden threats such as explosives, weapons, chemicals and drugs that are hidden in the target (e.g. inside a bag or under an individual's clothing); and the LiDAR system can provide distance information of the target that contains the threat. By fusing/combining the VIS, THz, and LiDAR images together, and using automated analysis of the fused/combined images through, e.g., deep learning technique, the system can provide a comprehensive and intelligent surveillance system for public security applications by 3D visualization and prediction of hidden threats.

Figure 4:
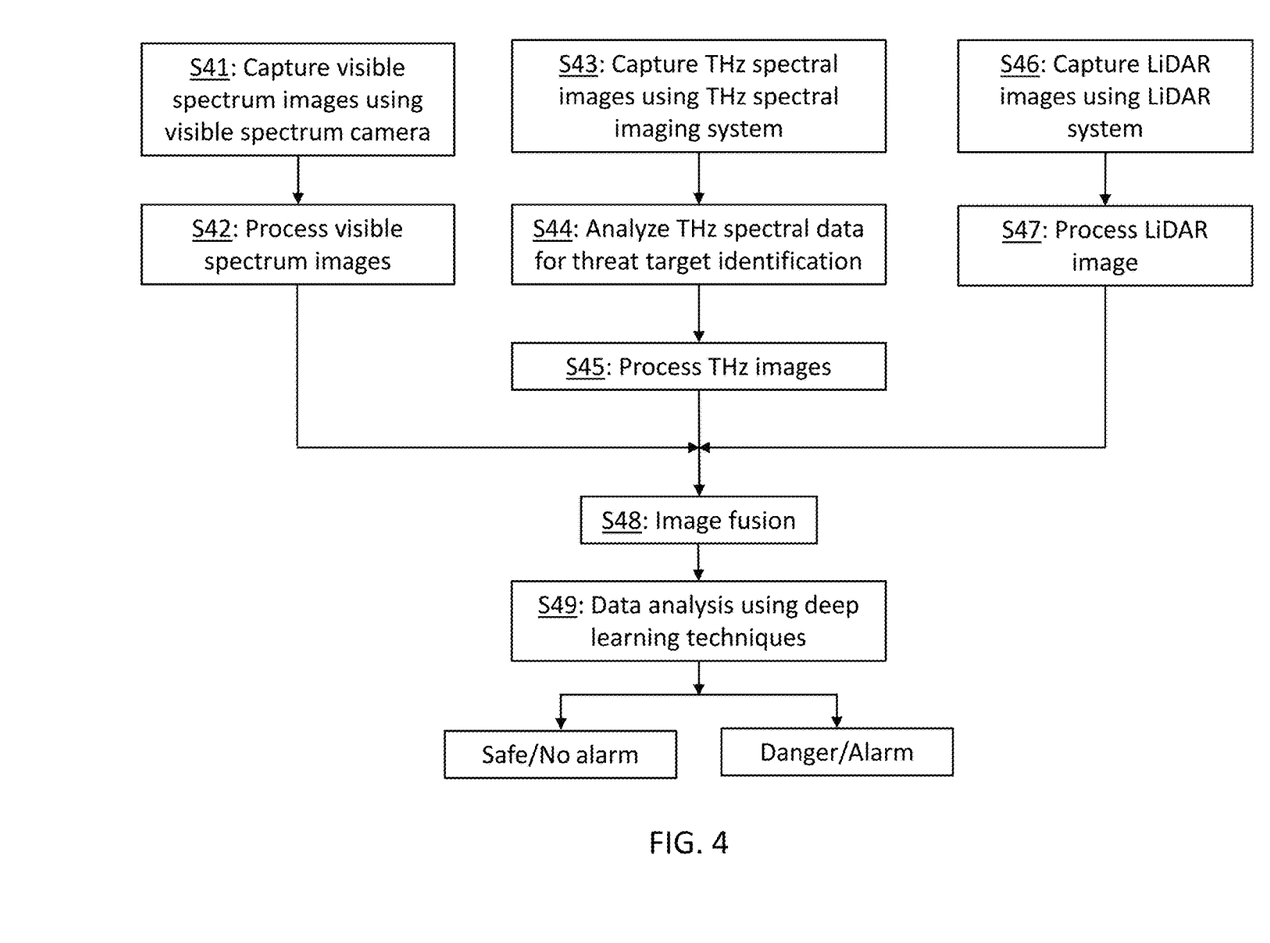
FIG. 4 schematically illustrates an operation of the intelligent security surveillance system of the embodiment of FIG. 3.

FIG. 4 schematically illustrates a process carried out by the intelligent security surveillance system. Steps S41, S43 and S46 perform capture of VIS images, THz spectral images, and LiDAR images using the respective imaging systems.

Step S44 performs a spectral analysis of the THz spectral images to identify specific security threats such as explosives, weapons, chemical and biological agents, etc. In this step, the THz spectral image data, consisting of a series of 2D images corresponding to different THz frequencies, is analyzed to identify any characteristic spectral features (i.e. shape of the intensity vs. THz frequency curve) present for each area (e.g. pixel or group of pixels) of the image. For this purpose, a database of THz spectra of various materials of interest such as explosives, weapons (metal), chemical and biological agents, etc. is provided in the central control and data processing system 34. The spectral curves obtained from the THz spectral images are compared to the spectra in the database to identify characteristic spectral features corresponding to any materials of interest. Thus, threats can be identified based on such analysis and the locations of the threats in the image can be determined. A processed THz image may be generated to indicate areas where security threats are present. For example, the processed THz image may contain the outline of a person with an area on the person marked as containing a threat.

Then, desired pre-processing is then performed for the VIS images, the processed THz images, and the LiDAR images in steps S42, S45 and S47, respectively. This may include, for example, cropping, scaling, adjusting contrast, other image enhancement treatment, etc. In step S48, the images of the same scene from the three imaging systems (VIS, THz (processed), and LiDAR) are fused, e.g., superimposed on each other, to help visualizing the target and the detected threats. Any suitable algorithm may be used to fuse the images. For example, the method described in Kowalski et al. 2013 may be used to fuse a VIS image and a processed THz image together. The fused VIS and THz image can be further fused with the LiDAR image. The fused image can be used to visualize the presence of threats hidden in a target, as well as the target's distance.

The fused image data may be displayed to a human operator for visualization, who will interpret the image and predict possible action by the target. However, this is slow and cannot meet the demand of security surveillance. Therefore, automated analysis of the fused images by computers for threat detection is highly desirable.

A challenge in automatic analysis is that image fusion produces a large volume of graphic data and conventional machine learning may be difficult to produce a real-time prediction. Thus, in the intelligent security surveillance system according to embodiments of the present invention, a deep learning technique, in particular one employing convolutional neural networks (CNNs), is used to obtain a real-time prediction from the image data set produced by image fusion (step S49). Using this technique, the neural network is trained to recognize threats present in the scene as well as the behavior patterns of persons associated with the threats. Training of the neural network is done by feeding training data into the neural network, the training data being in the form of fused images labeled with the types of threats present and behavior patterns.

Artificial neural networks are used in various fields such as machine leaning, and can perform a wide range of tasks such as computer vision, speech recognition, etc. An artificial neural network is formed of interconnected layers of nodes (neurons), where each neuron has an activation function which converts the weighted input from other neurons connected with it into its output (activation). In a learning process, training data are fed into to the artificial neural network and the adaptive weights of the interconnections are updated through the leaning process. After learning, data can be inputted to the network to generate results (referred to as prediction). A convolutional neural network (CNN) is a type of feed-forward artificial neural network; it is useful particularly in image recognition. Inspired by the structure of the animal visual cortex, a characteristic of CNNs is that each neuron in a convolutional layer is only connected to a relatively small number of neurons of the previous layer. More specifically, a filter is convolved across the previous layer to generate an activation map. This contributes to the translational invariance of CNNs. The general characteristics, architecture, configuration, training methods, etc. of CNNs are well described in the literature. Various specific CNNs models have been described as well.

For example, open source CNNs are available and may be adapted to implement the task of interpreting fused image data to generate real-time prediction in step S49 of the present embodiment. One example is Caffe, developed by Berkeley AI Research (BAIR) and by community contributors, which is a framework made with expression, speed, and modularity in mind. Another example is TensorFlow, developed by Google, which is an open source software library for numerical computation using data flow graphs. Nodes in the graph represent mathematical operations, while the graph edges represent the multidimensional data arrays (tensors) communicated between them.

Using deep leaning techniques, the machine learning component of the intelligent security surveillance system of this embodiment can learn various criminal/terrorist behavior patterns and make threat prediction based on the fused image from the VIS, THz and LiDAR imaging systems.

Compared with existing threat detection system such as that described in U.S. Pat. Appl. Pub. No. 2014/0028457 and Kowalski et al. 2013, cited earlier, the intelligent security surveillance system according to embodiments of the present invention offers the following advantages: First, using THz spectral imaging system significantly enhances the selectivity and specificity of the threat detection, and may also allow differentiative detection of multiple different threat agents (such as explosives, weapons, and drugs). Second, including a LiDAR in the security surveillance system allows accurate distance information of the potential threat to be obtained. Third, by combining deep learning of various criminal/terrorist behavior patterns present in the fused images, this intelligent security surveillance system will be able to accurately predict potentially dangerous persons/objects with hidden threats, thereby reducing false alarms. It will be apparent to those skilled in the art that various modification and variations can be made in the THz spectral imaging system, the intelligent security surveillance system, and related operating methods of the present invention without departing from the spirit or scope of the invention. Thus, it is intended that the present invention cover modifications and variations that come within the scope of the appended claims and their equivalents.

What is claimed is:

1. A terahertz (THz) spectral imaging system, comprising:
    a THz 2-dimensional (2D) imaging camera;
    a tunable THz bandpass filter comprising:
        a visible or infrared (IR) light source for generating a visible or IR light;
        a spatial light modulator receiving the visible or IR light and modulating it to generate spatially structured light patterns; and
        a semiconductor plate,
        wherein the spatial light modulator projects the light patterns onto the semiconductor plate, wherein the light pattern is configured to photo-generate carriers in the semiconductor plate to form a metamaterial THz bandpass filter in the semiconductor plate, the metamaterial THz bandpass filter being a metamaterial structure having a predefined transmission spectrum in a THz wavelength range; and
    a control device coupled to the THz 2D imaging camera and the tunable THz bandpass filter,
    wherein the semiconductor plate is disposed in front of the THz 2D imaging camera to filter the THz light before it is received by the THz 2D imaging camera, and
    wherein the control device is configured to control the spatial light modulator to generate a plurality of different predefined light patterns each corresponding to a different predefined transmission spectrum of the metamaterial THz bandpass filter, and to control a timing sequence of the spatial light modulator and the THz 2D imaging camera to acquire a plurality of 2D THz images corresponding to the plurality of predefined light patterns projected on the semiconductor plate.

2. The THz spectral imaging system of claim 1, further comprising a broadband THz light source for generating a broadband THz light for illuminating a target being detected, and wherein the tunable THz bandpass filter and the THz 2D imaging camera are disposed to receive the THz light reflected by or transmitted through the target.

3. The THz spectral imaging system of claim 2, wherein the controller is configured to control the broadband THz light source and the spatial light modulator according to the timing sequence to operate in a pulsed mode.

4. The THz spectral imaging system of claim 1, wherein the semiconductor plate is a silicon plate.

5. The THz spectral imaging system of claim 1, wherein each light pattern generated by the spatial light modulator includes an array of periodic elements having sizes in a range of nanometers to millimeters, and wherein the controller is configured to change one or more of a size, a shape and a period of the array of periodic elements to generate the plurality of predefined light patterns.

6. The THz spectral imaging system of claim 5, wherein the elements of the light pattern have a cross shape.

7. A tunable terahertz (THz) bandpass filter comprising:
    a visible or infrared (IR) light source for generating a visible or IR light;
    a spatial light modulator receiving the visible or IR light and modulating it to generate spatially structured light patterns; and
    a semiconductor plate,
    wherein the spatial light modulator projects the light patterns onto the semiconductor plate, wherein the light pattern is configured to photo-generate carriers in the semiconductor plate to form a metamaterial THz bandpass filter in the semiconductor plate, the metamaterial THz bandpass filter being a metamaterial structure having a predefined transmission spectrum in a THz wavelength range; and
    wherein the spatial light modulator is configured to be controlled by an external control device to generate a plurality of different light patterns to form different metamaterial THz bandpass filters with different predefined transmission spectra in the semiconductor plate.

8. The tunable THz bandpass filter of claim 7, wherein the semiconductor plate is a silicon plate.

9. The tunable THz bandpass filter of claim 7, wherein each light pattern the spatial light modulator includes an array of periodic elements having sizes in a range of nanometers to millimeters, and different light patterns are different in at least one of a size, a shape and a period of the array of periodic elements.

10. The tunable THz bandpass filter of claim 9, wherein the elements of the light pattern have a cross shape.

11. A security surveillance system comprising:
    a visible light imaging camera generating visible light images;
    a terahertz (THz) spectral imaging system generating a plurality of 2-dimensional (2D) THz images each based on THz light of a different frequency range, the THz spectral imaging system including:
        a THz 2-dimensional (2D) imaging camera;
        a tunable THz bandpass filter; and
        a control device coupled to the THz 2D imaging camera and the tunable THz bandpass filter,
        wherein the tunable THz bandpass filter has a filter plate disposed in front of the THz 2D imaging camera to filter the THz light before it is received by the THz 2D imaging camera, and wherein the control device is configured to tune a transmission spectrum of the tunable THz bandpass filter, and to control the tuning of the tunable THz bandpass filter and the THz 2D imaging camera according to a predetermined timing sequence, to generate the plurality of 2D THz images each based on THz light of a different frequency range;

a Light Detection and Ranging (LiDAR) system generating LiDAR images representing distances of objects from a sensor of the LiDAR system;

a central control and data processing system; and an alarm system, where the central control and data processing system is coupled to the visible light imaging camera, the THz spectral imaging system, the LiDAR system and the alarm system, and is configured to: perform spectral analysis of the 2D THz images to generate processed THz image indicating presence of any one of a plurality of predefined materials, fuse the visible light images, the processed THz images and the LiDAR images into a fused image, and automatically analyze the fused image using machine learning to generate an alarm based on learned behavior patterns of targets in the fused image.

12. The security surveillance system of claim 11, further comprising a display coupled to the central control and data processing system for displaying one or more of: the visible light images, the processed THz images, the LiDAR images, and the fused image.

13. The security surveillance system of claim 11, wherein the central control and data processing system stores a database of THz spectra of the plurality of predefined materials, and performs the spectral analysis of the THz images by generating a THz spectrum of each area of the THz image and comparing the THz spectrum with the spectra stored in the database.

14. The security surveillance system of claim 11, wherein the tunable THz bandpass filter comprises:

a visible or infrared (IR) laser light source for generating a visible or IR light;

a spatial light modulator receiving the visible or IR light and modulating it to generate spatially structured light patterns; and a semiconductor plate, wherein the spatial light modulator projects the light patterns onto the semiconductor plate, wherein the light pattern is configured to photo-generate carriers in the semiconductor plate to form a metamaterial THz bandpass filter in the semiconductor plate; and wherein the control device is configured to control the spatial light modulator to generate a plurality of predefined light patterns each corresponding to a transmission spectrum of the semiconductor plate, and to control a timing sequence of the spatial light modulator and the THz 2D imaging camera to acquire the plurality of 2D THz images.

15. The security surveillance system of claim 11, wherein the LiDAR system is a scanning LiDAR system.

16. The security surveillance system of claim 11, wherein the LiDAR system is a solid-state LiDAR system.

* * * * *